United States Patent [19]

Krstenansky

[11] Patent Number: 5,395,823
[45] Date of Patent: Mar. 7, 1995

[54] NEUROPEPTIDE Y AGONISTS AND PARTIAL AGONISTS

[75] Inventor: John L. Krstenansky, Cincinnati, Ohio

[73] Assignee: Merrell Dow Pharmaceuticals Inc., Cincinnati, Ohio

[21] Appl. No.: 32,526

[22] Filed: Mar. 15, 1993

Related U.S. Application Data

[63] Continuation of Ser. No. 925,546, Aug. 5, 1992, abandoned, which is a continuation of Ser. No. 782,890, Oct. 18, 1991, abandoned, which is a continuation of Ser. No. 631,755, Dec. 21, 1990, abandoned, which is a continuation of Ser. No. 384,373, Jul. 24, 1989, abandoned, which is a continuation-in-part of Ser. No. 237,591, Aug. 26, 1988, abandoned.

[51] Int. Cl.$^6$ .................... A61K 38/00; C07K 5/00; C07K 7/00; C07K 14/00
[52] U.S. Cl. .................................. 514/12; 514/9; 514/11; 530/300; 530/317; 530/321; 530/324
[58] Field of Search ............... 530/317, 321, 324, 300; 514/12, 11, 9

[56] References Cited

U.S. PATENT DOCUMENTS

| | | | |
|---|---|---|---|
| 4,355,025 | 11/1982 | Lazarus | 530/324 |
| 4,701,441 | 11/1987 | Kalra | 514/12 |
| 4,808,701 | 2/1989 | Danho et al. | |
| 4,839,343 | 6/1989 | Waeber et al. | 514/12 |
| 4,891,357 | 1/1990 | Kalra | 514/12 |

FOREIGN PATENT DOCUMENTS 3811193 10/1989 Germany.

OTHER PUBLICATIONS

Beck et al., FEBS Letters, vol. 244, No. 1, Feb. 1989, pp. 119–122.
Tatemoto, K., "Neuropeptide Y: Complete amino acid sequence of the brain peptide," Proc. Natl. Acad. Sci. USA, Biochemistry, vol. 79, pp. 5485–5489, 1982.
Beck, A., et al., "Highly potent and small neuropeptide Y agonist obtained by linking NPY 1–4 via spacer to α-helical NPY 25–36", 6096 FEBS Letters, 244, No. 1, 1989.
Krstenansky, J. L., et al., "Centrally truncated and stabilized porcine neuropeptide Y analogs: Design, synthesis and mouse brain receptor binding," Proc. Natl. Acad. Sci USA, Biochemistry, vol. 86, pp. 4377–4381, 1989.
Boublik, J., et al., "Neuropeptide Y and neuropeptide $Y_{18-36}$", Int. J. Peptide Protein Res. 33, 11–15 (1989).
Boublik, J. H., "Synthesis and Hypertensive Activity of Neuropeptide Y Fragments and Analogues with Modified N-or C-Termini or D-Sustitutions", J. Med. Chem. 32(3), 597–601(1989).
Cox, et al., Peptides vol. 12:323–327 (1991).
Dockray, G. J., Neuropeptide Y: In Search of a Function, Neurochem. Int. 8(1), 9–11 (1986).
Maccarrone, C. and Jarrott, B., Neuropeptide Y: A Punitive Neurotransmitter, Neurochem. Int. 8(1), 13–22 (1986).
J. M. Danger, et al., Life Sciences, vol. 40, No. 19 pp. 1875–1880, (1987).
Martel, et al., Peptides 7, pp. 55–60 (1986).
Rioux, et al., Peptides 7, pp. 27–31 (1986).
J. M. Allen, et al., Neurochem. Int. vol. 8, No. 1, pp. 1–8 (1986).
"Peptide Neuroregulation of Vascular Tone by the Sympathetic nervous System", Elsevier Science Publishers B. V., Amsterdam pp. 383–384 (1986).
J. M. Lundberg, et al., European Journal of Pharmacology, 145, pp. 21–29, (1988).
J. G. Clarke, et al., The Lancet, 1057–1059, (1987).
A. Balasubramaniam, et al. Int. J. Peptide protein Res. 29, 78–83 (1987).
T. Mochizuki et al., Peptide Chemicstry 20: 59–64 (1982).
J. L. Krstenansky, et al., Neuropeptides 10, 77–85 (1987).

Primary Examiner—Jill Warden
Assistant Examiner—A. M. Davenport
Attorney, Agent, or Firm—Kenneth J. Collier

[57] ABSTRACT

Agonists of NPY which are derivatives of naturally occurring NPY. The agonism is confirmed using conventional competitive binding and biochemical assays and the use of these derivatives in a variety of conditions in which neuropeptide Y is implicated is also described.

9 Claims, No Drawings

NEUROPEPTIDE Y AGONISTS AND PARTIAL AGONISTS

CROSS REFERENCE TO RELATED APPLICATION

This is a continuation of application Ser. No. 07/925,546, filed Aug. 5, 1992, now abandoned; which is a continuation of application Ser. No. 07/782,890, filed Oct. 18, 1991, (now abandoned); which is a continuation of application Ser. No. 07/631,755, filed Dec. 21, 1990, (now abandoned); which is a continuation of application Ser. No. 07/384,373, filed Jul. 24, 1989 (now abandoned); which is a continuation-in-Part of application Ser. No. 07/237,591, filed Aug. 26, 1989, (now abandoned).

FIELD OF THE INVENTION

This invention relates to novel peptide derivatives which are agonists of neuropeptide Y.

BACKGROUND OF THE INVENTION

Porcine neuropeptide Y (pNPY) is a 36 amino acid residue peptide that belongs to a unique family of peptides having a wide distribution throughtout the central and peripheral nervous systems. Receptors for NPY are found in the central nervous system and in the periphery. In the brain, NPY is a potent stimulator of food intake, stimulates leutinizing hormone, growth hormone and prolactin, and produces cardiovascular depression. NPY is also a potent peripheral vasoconstrictor and has been reported to cause transient myocardial ischaemia in patients with angina pectoris. Agents which are agonists of these receptors are expected to increase appetite, decrease sexual behavior, decrease thyroid stimulating hormone, prolactin, leutenizing hormone and therefore would be useful as contracptive agents, to diminish sex drive in sex offenders, and in the treatment of reproductive-system related disorders, such as precocious puberty, endometriosis, breast tumors, prostate tumors, and decrease growth hormone levels by stimulating release and to act as peripheral vasodilators and therefore act as hypotensive agents. The compounds of this invention could be used in the treatment of eating disorders such as anorexia nervosa.

SUMMARY OF THE INVENTION

Novel petide derivatives of formulae 1-4

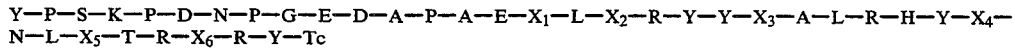

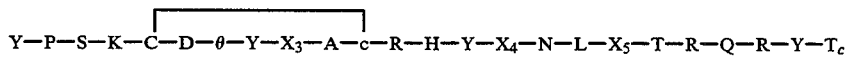

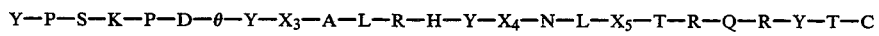

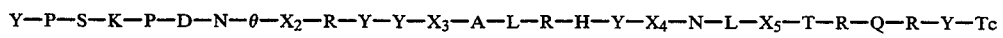

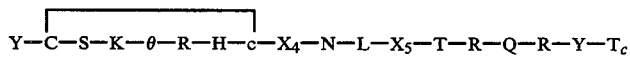

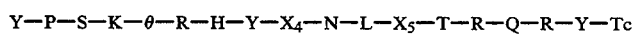

wherein $X_1$ is E or D;
$X_2$ is S or A;
$X_3$ is S or A;
$X_4$ is L, I, M, Nle, or V;
$X_5$ is L, I, M, Nle, or V;
$X_6$ is Q, P, H, or I;
Tc is OR' or NHR';
wherein R' is a hydrogen or a ($C_1$-$C_4$)alkyl group; $\theta$ is a group of the structural formula

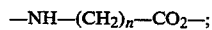

wherein n is an integer of from 1-11, and the pharmaceutically acceptable salts thereof are agonists of neuropeptide Y. These peptide derivatives increase blood pressure in warm blooded animals and are also useful in the treatment of eating disorders such as anorexia nervosa.

DETAILED DESCRIPTION OF THE INVENTION

The following common abbreviations of the amino acids and amino and carboxy terminal groups are used throughout this specification:
Ala (or A)—alanine
Val (or V)—valine
Leu (or L)—leucine
Ile (or I)—isoleucine
Pro (or P)—proline
Met (or M)—methionine
Ser (or S)—serine
Thr (or T)—threonine
Cys (or C)—cysteine
cys (or c)—D-cysteine
Tyr (or Y)—tyrosine
Asn (or N)—asparagine
Asp (or D)—aspartic acid
Lys (or K)—lysine
Arg (or R)—arginine
His (or H)—histidine
Glu (or E)—glutamate
Nle—norleucine
Aoc—8-aminooctanoic acid
——NH$_2$ An alkyl group is taken to include straight, branched, or cyclic alkyl groups, for example, methyl, ethyl, propyl, isopropyl, butyl, isobutyl, tert-butyl, pentyl, isopentyl, sec-pentyl, cyclopentyl, hexyl, isohexyl, cyclohexyl and cyclopentylmethyl. An acyl group of from 2 to 10 carbon atoms is taken to include straight, branched, cyclic, saturated and unsaturated acyl groups having 1 or 2 carbonyl moieties per group, for example, acetyl, benzoyl succinyl, maleyl, and glutaryl. Those peptides wherein the amino group of the amino terminal amino acid is substituted with two alkyl or acyl groups are also considered to be within the scope of the peptides of this invention.

The natural amino acids, with the exception of glycine, contain a chiral carbon atom. Unless otherwise specifically indicated, the optically active amino acids, referred to herein, are of the L-configuration.

The polypeptides of formula 1 can form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower)alkylpiperidine, and any other suitable amine.

As with any generic group of chemical compounds, certain groups are preferred. Applicants prefer those peptide derivatives of formula 1 wherein $X_1$ is glutamate (E). Applicants also prefer those peptide derivatives of formula 1 wherein $X_2$ and $X_3$ are independently serine (S) or alanine (A), as well as those peptide derivatives of formula 1 wherein $X_4$ or $X_5$ are independently leucine (L) or isoleucine (I) wherein Tc is $NH_2$ and wherein $\theta$ is Aoc. The most preferred peptide derivatives of formula 1-4 are the peptide derivative of formula 5-8, respectively.

the art. Such procedures include the solid phase sequential procedure which can be performed using established automated methods such as by use of an automated peptide sythesizer.

The resin support employed can be any suitable resin conventionally employed in the art for the solid phase preparation of polypeptides, preferably polystyrene which has been cross-linked with from 0.5 to about 3 percent divinyl benzene, which has been either converted to the p-methylbenzhydrylamine or benzhydrylamine derivative (for C-terminal amides) or chloromethylated or hydroxymethylated to provide sites for ester formation with the initially introduced α-amino protected amino acid (for producing C-terminal alkylamides and esters).

An example of a hydroxymethyl resin is described by Bodanszky, et al., *Chem. Ind. (London)* 38, 1597–98 (1966). A chloromethylated resin is commercially available from Bio Rad Laboratories, Richmond, Calif., and the preparation of such a resin is described by Stewart et al., "Solid Phase Peptide Synthesis" (Freeman & Co., San Francisco 1969), Chapter 1, pp. 1–6. The protected amino acid can be bound to the resin by the procedure of Gisin, *Helv. Chem Acta*, 56, 1476 (1973). Many resin bound, protected amino acids are commercially available. As an example, to prepare a polypeptide of this invention wherein the carboxy terminal end is a Thr residue, a tert-butyloxycarbonyl (Boc) protected Thr bound to a benzylated, hydroxymethylated phenylacetamidomethyl (PAM) resin can be used and is commercially available.

Following the coupling of the α-amino protected amino acid to the resin support, the protecting group is removed using any suitable procedure such as by using trifluoroacetic acid in methylene chloride, trifluoroacetic acid alone, or HCl in dioxane. The deprotection is carried out at a temperature of between 0° C. and room temperature. Other standard cleaving reagents and conditions for removal of specific α-amino protecting groups may be used. After removal of the α-amino protecting group the other amino protected amino acids are coupled step-wise in the desired order. Alternatively, multiple amino acid groups may be coupled by the solution method prior to coupling with the resin supported amino acid sequence.

The α-amino protecting group employed with each amino acid introduced into the polypeptide sequence may be any such protecting group known to the art. Among the classes of α-amino protecting groups con-

Y—P—S—K—P—D—N—P—G—E—D—A—P—A—E—E—L—S—R—Y—Y—A—A—L—R—H—Y—L—N—L—L—T—R—Q—R—Y—#     5

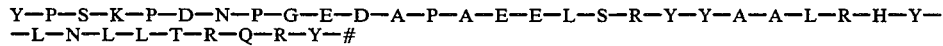

Y—P—S—K—C—D—Aoc—Y—S—A—c—R—H—Y—I—N—L—I—T—R—Q—R—Y—#     6

Y—P—S—K—P—D—AOC—Y—S—A—L—R—H—Y—I—N—L—I—T—R—Q—R—Y—#     6'

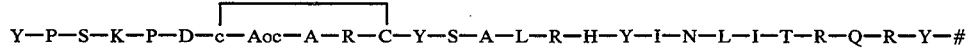

Y—P—S—K—P—D—c—Aoc—A—R—C—Y—S—A—L—R—H—Y—I—N—L—I—T—R—Q—R—Y—#     7

Y—P—S—K—P—D—N—Aoc—A—R—Y—Y—S—A—L—R—H—Y—I—N—L—I—T—R—Q—R—Y—#     7'

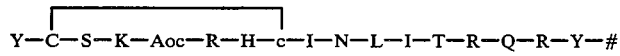

Y—C—S—K—Aoc—R—H—c—I—N—L—I—T—R—Q—R—Y—#     8

Y—P—S—K—Aoc—R—H—Y—I—N—L—I—T—R—Q—R—Y—#     8'

The proteins of this invention can be prepared by a variety of procedures readily known to those skilled in templated are (1) acyl type protecting groups such as: formyl, trifluoroacetyl, phthalyl, toluenesulfonyl (tosyl), benzenesulfonyl, nitro-phenylsulfenyl, tritylsulfenyl, o-nitrophenoxyacetyl and α-chlorobutyryl; (2) aromatic urethan type protecting groups such as benzyloxycarbonyl and substituted benzyloxycarbonyl, such as p-chlorobenzyloxycarbonyl, p-nitrobenzyl- carbonyl, p-bromobenzyl-oxycarbonyl, p-methoxybenzyloxycarbonyl, 1-(p-biphenylyl)-1-methylethoxycarbonyl, α,α-dimethyl-3,5-dimethoxybenzyloxycarbonyl, benzhydryloxycarbonyl and 9-fluorenylmethoxycarbonyl (Fmoc); (3) aliphatic urethan protecting groups such as tert-butyloxycarbonyl (Boc), diisopropylmethoxycarbonyl, isopropyloxycarbonyl, ethoxycarbonyl and allyloxycarbonyl; (4) cycloalkyl urethan type protecting groups such as cyclopentyloxycarbonyl, adamantyloxycarbonyl and cyclohexyloxycarbonyl; (5) thio urethan type protecting groups such as phenylthiocarbonyl; (6) alkyl type protecting groups such as triphenylmethyl (trityl) and benzyl; and (7) trialkylsilane groups such as trimethylsilane. The preferred α-amino protecting group is tert-butyloxycarbonyl or Fmoc.

The selection of an appropriate coupling reagent is within the skill of the art. A particularly suitable coupling reagent where the amino acid to be added is Gln, Asn or Arg is N,N'-diisopropylcarbodiimide and 1-hydroxy-benzotriazole. The use of these reagents prevents nitrile and lactam formation. Other coupling agents are (1) carbodiimides (e.g., N,N'-dicyclohexylcarbodiimide and N-ethyl-N'-(γ-dimethylaminopropyl-carbodiimide); (2) cyanamides (e.g., N,N-dibenzylcyanamide); (3) ketenimines; (4) isoxazolium salts (e.g., N-ethyl-5-phenyl-isoxazolium-3'-sulfonate; (5) monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyl-di-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., (Boc-Ala)$_2$—O) and (8) nitrogen containing heterocyclic compounds having a hydroxy group on one ring nitrogen (e.g., N-hydroxyphthalimide, N-hydroxysuccinimide and 1-hydroxybenzotriazole). Other activating reagents and their use in peptide coupling are described by Kapoor, *J. Pharm. Sci.*, 59, pp. 1–27 (1970). Applicants prefer the use of the symmetrical anhydride as a coupling reagent for all amino acids except Arg, Asn and Gln.

Each protected amino acid or amino acid sequence is introduced into the solid phase reactor in about a fourfold excess and the coupling is carried out in a medium of dimethylformamide: methylene chloride (1:1) or in dimethylformamide alone or preferably methylene chloride alone. In cases where incomplete coupling occurs, the coupling procedure is repeated before removal of the α-amino protecting group, prior to the coupling of the next amino acid in the solid phase reactor. The success of the coupling reaction at each stage of the synthesis is monitored by the ninhydrin reaction as described by E. Kaiser et al, *Analyt. Biochem.* 34, 595 (1970).

After the desired amino acid sequence has been obtained, the peptide is removed from the resin. This can be done by hydrolysis such as by treatment of the resin bound polypeptide with a solution of dimethyl sulfide, p-cresol and thiocresol in liquid hydrofluoric acid.

As is known in the art of solid phase peptide synthesis many of the amino acids bear functionalities requiring protection during the chain preparation. The use and selection of the appropriate protecting group is within the ability of those skilled in the art and will depend upon the amino acid to be protected and the presence of other protected amino acid residues on the peptide. The selection of such a side chain protecting group is critical in that it must be one which is not removed during cleavage of the protecting group of the α-amino moiety. For example, suitable side chain protecting groups for lysine are benzyloxycarbonyl and substituted benzyloxycarbonyl, said substituent being selected from halo (e.g., chloro, bromo, fluoro) and nitro (e.g., 2-chlorobenzyloxycarbonyl, p-nitrobenzyloxy-carbonyl, 3,4-dichlorobenzyloxycarbonyl), tosyl, t-amyloxycarbonyl, t-butyloxycarbonyl and diisopropylmethoxycarbonyl. The alcoholic hydroxyl group of threonine and serine can be protected with an acetyl, benzoyl, tert-butyl, trityl, benzyl, 2,6-dichlorobenzyl or benzyloxycarbonyl group. The carboxylic group of Aspartic acid and Glutamic acid can be protected with a benzyl or cyclohexyl group. The preferred protecting group is benzyl.

These groups can be removed by procedures well known in the art. Typically protecting group removal is done after the peptide chain synthesis is complete but the protecting groups can be removed at any other appropriate time.

The ability of the peptide derivatives of formula 1 to act as agonists of neuropeptide Y can be demonstrated by the ability of such peptides to compete with iodinated neuropeptide Y for receptors using the method of Lundberg et al. *Eur. J. Pcol.* 145:21–9 (1988). $^{125}$I-Bolton-Hunter-neuropeptide Y (BHNPY; Amersham) binding was carried out in porcine spleen crude membranes. Membranes from frozen spleen were prepared as described previously for tachykinin peptide binding studies (Buck et al., 1984). An aliquot of membrane preparation (approximately 15 mg tissue) was incubated at room temperature for 2 hr in buffer (pH 7.4) containing the peptide analog, 130 mM NaCl, 2.7 mM KCl, 2 mM MgCl$_2$, 1.8 mM CaCl$_2$, 20 mM HEPES, 4 mg/ml BSA, 40 μg/ml bacitracin, 4 μg/ml leupeptin and 4 μg/mol chymostatin. BHNPY was included in a concentration of 0.1 nM and non-specific binding was determined by the inclusion of 1 μM pNPY. Samples were rapidly filtered over Whatman GF/C filters presoaked overnight in 0.5% histone (type II-AS; Sigma) and washed two times with ice-cold, plain HEPES-salt buffer (pH 7.4). IC$_{50}$ values for test peptides were calculated from 6 to 10 point competition curves. Utilizing this procedure the peptide derivatives of Examples 1 and 2 were found to have an IC$_{50}$ of <50 nM.

By virtue of the ability of the peptide derivatives of this invention to act as agonists of neuropeptide Y, the compounds possess valuable pharmacologic properties such as hypertensive activity as well as vasoconstricting activity and constricting of the coronary artery, colon relaxing activity, and gastric emptying diminution. Significant medical uses of the NPY agonists of this invention are in the treatment of eating disorder such as anorexia nervosa.

The dose of a peptide derivative of this invention required to agonize neuropeptide Y and therefore produce a hypertensive or vasoconstricting and other effects is from 0.2 mg/kg to 250 mg/kg of patient body weight per day depending on the patient, the severity of the condition to be treated and the peptide derivative selected. The suitable dose for a particular patient can be readily determined. Preferably from 1 to 4 daily doses would be administered typically with from 5 mg to 100 mg of active compound per dose.

The term "patient" used herein is taken to mean mammals such as primates, including humans, sheep, horses, cattle, pigs, dogs, cats, rats and mice.

Although some of the peptide derivatives may survive passage through the gut following oral administration, applicants prefer non-oral administration, for example, subcutaneous, intravenous, intramuscular or intraperitoneal; administration by depot injection; by implant preparation; or by application to the mucous membranes, such as, that of the nose, throat and bronchial tubes, for example, in an aerosol can containing a peptide derivative of this invention in a spray or dry powder form.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

EXAMPLES

This invention is illustrated by the following, nonlimiting examples.

EXAMPLE 1

Preparation of
Y—P—S—K—P—D—N—P—G—
E—D—A—P—A—E—
E—L—S—Y—Y—A—A—L—R—H—Y—L—N—L-
—L—T—R—Q—R—Y—#

The title peptide derivative was synthesized on a 0.5 mmol scale by solid-phase methods on p-methylbenzhydrylamine resin (0.40 mmol/g; Peptides Intl.) using an Applied Biosystems Model 430-A Peptide Synthesizer. All residues were double coupled as the symmetrical anhydrides of the $N^\alpha$-t-Boc-protected amino acids with the exception of Arg, Asn and Gln which were double coupled by the DCC/HOBT methodology. The side chain protection was as follows: Arg(Tos), Asp(Chx), Cys(pMeBzl), Glu(Bzl), His(Tos), Ser(Bzl), Tyr(2-BrZ), Thr(Bzl), Lys(2-ClZ). The peptides (0.25 mmol theory) were cleaved from the resin support and deprotected in liquid HF containing 5% anisole at −5° C. for 40 min. After removal of the HF in vacuo the peptide was extracted from the resin with 30% acetic acid and water. The solution was filtered from the resin and lyophilized. The peptidic material that remained was purified by preparative HPLC on a Dynamax C-18 column (41.4×250 mm; Rainin) using acetonitrile in 0.1% trifluoroacetic acid as an eluant. The purity and identity of the peptide were assessed by analytical HPLC (Vydac 218TP54 column, 4.6 c×250 mm, 2.0 ml/min, $t_c$ − 1.9 min, linear gradient of 15–40% acetonitrile in 0.1% TFA over 25 min), amino acid analysis (AAA)(6N HCl containing 8% phenol; 106° C.; 20 and 40 hr), and fast atom bombardment-mass spectrometry (FAB-MS)(M-Scan Ltd.).

AAA$^a$: B-1.96; T-1.03; S-1.62; P-1.88; A-1.96; I-2.84; L-2.14; Y-4.04; H-1.09; R-4.06.

$^a$6N HCl, 24 Hr, 106° C.

FAB-MS (M+H)+ 3311.2±1 mu.

EXAMPLE 2

Preparation of

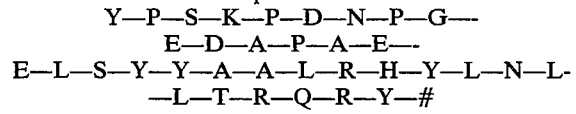

Y—P—S—K—C—D—Aoc—Y—S—A—c—R—H—Y—I—N—L—I—T—R—Q—R—Y—#

The title peptide derivative was synthesized on a 0.5 mmol scale by solid-phase methods on p-methylbenzhydrylamine resin (0.40 mmol/g; Peptides Intl.) using an Applied Biosystems Model 430-A Peptide Synthesizer. All residues were double coupled as the symmetrical anhydrides of the $N^\alpha$-t-Boc-protected amino acids with the exception of Arg, Asn and Gln which were double coupled by the DCC/HOBT methodology. The side chain protection was as follows: Arg(Tos), Asp(Chx), Cys(pMeBzl), Glu(Bzl), His(ToS), Ser(Bzl), Tyr(2-BrZ), Thr(Bzl), Lys(2-ClZ). The peptides (0.25 mmol theory) were cleaved from the resin support and deprotected in liquid HF containing 5% anisole at −5° C. for 40 min. After removal of the HF in vacuo the peptide was extracted from the resin with 30% acetic acid and water. The extract was diluted to 1 liter, the pH adjusted to between 8 and 9 with ammonium hydroxide and 0.01 N potassium ferricyanide was added until a yellow color persisted (approx. 25 ml). After stirring for 30 min, the pH was lowered to <5 with glacial acetic acid and the solution was stirred with 25 ml of settled AC 3×4A resin (Bio Rad) for 2 hours. The solution was filtered from the resin and lyophilized. The peptidic material that remained was purified by preparative HPLC on a Dynamax C-18 column (41.4×250 mm; Rainin) using acetonitrile in 0.1% trifluoroacetic acid as an eluant. The purity and identity of the peptide were assessed by analytical HPLC (Vydac 218TP54 column, 4.6 c×250 mm, 2.0 ml/min, $t_c$ − 1.9 min, linear gradient of 15–40% acetonitrile in 0.1% TFA over 25 min), amino acid analysis (AAA)(6N HCl containing 8% phenol; 106° C.; 20 and 40 hr), and fast atom bombardment-mass spectrometry (FAB-MS)(M-Scan Ltd.).

AAA$^a$: B-1.89; T-0.99; S-1.68; Z-1.13; P-0.93; A-1.03; L-1.09; I-2.07; Y-3.88; H-0.94; R-3.06.

$^a$6N HCl, 24 Hr, 106° C.

FAB-MS 2888.0±1 mu.

EXAMPLE 3

Preparation of

Using substantially the procedure of Example 2, the title compound was prepared.

AAA$^a$: B-2.03; T-1.05; S-1.83; Z-1.10; P-1.98; A-2.04; L-2.07; I-1.93; Y-3.91; K-1.02; H-0.98; R-3.87.

$^a$6N HCl, 24 Hr, 106° C.

FAB-MS 3327±1 mu.

EXAMPLE 4

Preparation of

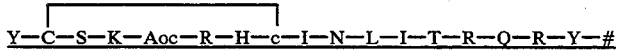

Using substantially the procedure of Example 2, the title compound was prepared.

AAA$^a$: B-1.00; S-1.00; T-1.01; Z-1.03; L-0.99; I-1.86; Y-2.06; H-0.97; R-2.97; K-1.10.

$^a$6N HCl, 24 Hr, 106° C.

FAB-MS 2193±mu.

In a like manner compounds of Examples 5-12 are prepared.

Compounds of examples 5-12 have the following characteristics:

|    | MW calcd | (M + H) | Ellman |
|----|----------|---------|--------|
| 5  | 3293.7   | 3295.3  | neg    |
| 6  | 3333.7   | 3334.2  | neg    |
| 7  | 4220.1   | 4220.8  |        |
| 8  | 4260.1   | 4262.4  |        |
| 9  | 1478.9   | 1480.0  |        |
| 10 | 3397.8   | 3398.9  |        |
| 11 | 1976.0   | 1978.4  | neg    |
| 12 | 4236.2   | 4236.2  |        |

|    | B       | T       | S       | Z       | P       | A       | G       | I       | L       | Y       | F       | H       | K       | R       |
|----|---------|---------|---------|---------|---------|---------|---------|---------|---------|---------|---------|---------|---------|---------|
| 5  | 2.03(2) | 1.04(1) | 1.82(2) |         | 2.95(3) | 2.06(2) |         | 1.98(2) | 2.02(2) | 3.91(4) |         | 0.99(1) | 1.00(1) | 4.02(4) |
| 6  | 2.05(2) | 1.07(1) | 1.78(2) |         | 1.86(2) | 2.01(2) |         | 1.96(2) | 2.12(2) | 3.81(4) |         | 2.02(2) | 1.03(1) | 4.06(4) |
| 7  | 5.07(5) | 0.99(1) | 1.86(2) | 2.11(2) | 5.10(5) | 4.20(4) | 1.34(1) | 1.81(2) | 3.02(3) | 4.74(5) |         | 0.97(1) | 1.03(1) | 3.95(4) |
| 8  | 5.43(5) | 0.96(1) | 1.69(2) | 2.00(2) | 3.88(4) | 4.68(5) | 1.37(1) | 1.93(2) | 3.24(3) | 5.08(5) |         | 1.94(2) | 0.87(1) | 4.11(4) |
| 9  | 1.03(1) | 1.01(1) |         | 1.05(1) |         |         |         | 1.91(2) | 1.01(1) | 1.93(2) |         |         |         | 2.06(2) |
| 10 | 2.65(3) | 1.03(1) | 1.96(2) | 1.08(1) | 2.08(2) | 2.09(2) |         | 1.95(2) | 2.15(2) | 5.04(5) |         | 1.01(1) | 1.06(1) | 3.84(4) |
| 11 | 1.01(1) | 1.05(1) |         | 1.07(1) |         |         |         | 1.92(2) | 0.99(1) | 2.04(2) |         | 0.97(1) |         | 2.96(3) |
| 12 | 4.92(5) | 1.00(1) | 1.80(2) | 2.01(2) | 3.94(4) | 4.12(4) | 1.27(1) | 2.65(3) | 3.01(3) | 4.68(5) |         | 0.96(1) | 0.96(1) | 3.73(4) |

I claim:

1. A peptide derivative of the formulae

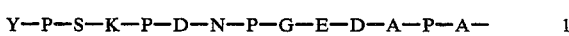

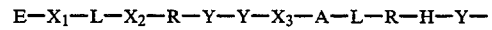

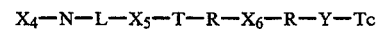

Ex.

5

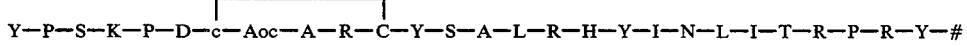

6

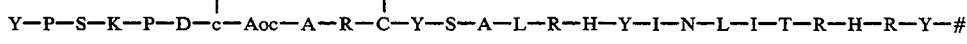

7

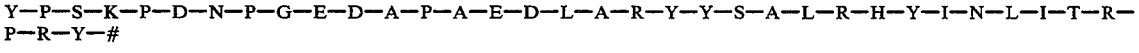

8

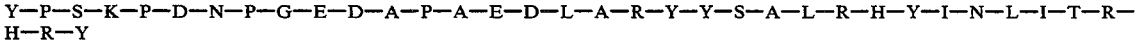

9  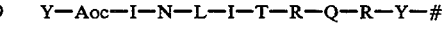

10  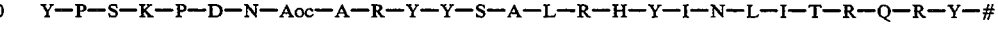

11

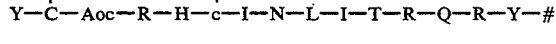

12

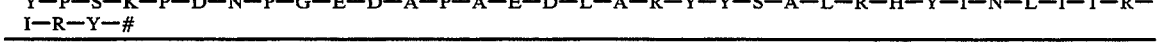

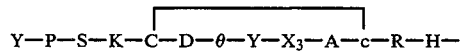

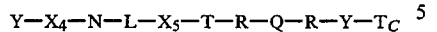

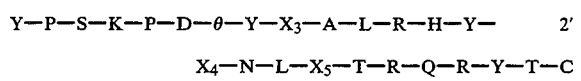

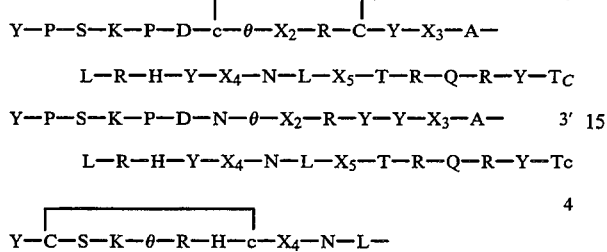

wherein
X₁ is E;

X₂ is S or A;
X₃ is S or A;
X₄ is L, or I;
X₅ is L, or I;
X₆ is Q, P, or H;
Tc is OR' or NHR';
wherein R' is a hydrogen or a (C₁-C₄)alkyl group;
θ is a group of the structural formula $$-NH-(CH_2)_n-CO_2-;$$

wherein n is an integer of from 1-11 or a pharmaceutically acceptable salt thereof.

2. A peptide derivative of claim 1 wherein X₂ is A.
3. A peptide derivative of claim 1 wherein X₃ is S.
4. A peptide derivative of claim 1 wherein X₄ is I.
5. A peptide derivative of claim 1 wherein X₅ is I.
6. A peptide derivative of claim 1 wherein X₆ is Q.
7. A peptide derivative of claim 1 wherein θ is Aoc.
8. A peptide derivative of claim 1 which is

Y—P—S—K—P—D—N—P—G—E—D—A—P—A—E—E—L—S—R—Y—Y—A—A—L—R—H—Y—L—N—L—L—T—R—Q—R—Y—#

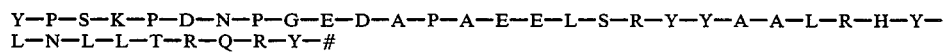

Y—P—S—K—P—D—Aoc—Y—S—A—L—R—H—Y—I—N—L—I—T—R—Q—R—Y—#

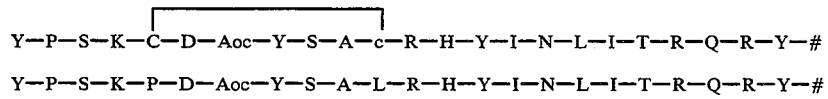

Y—P—S—K—P—D—N—Aoc—A—R—C—Y—S—A—L—R—H—Y—I—N—L—I—T—R—Q—R—Y—H

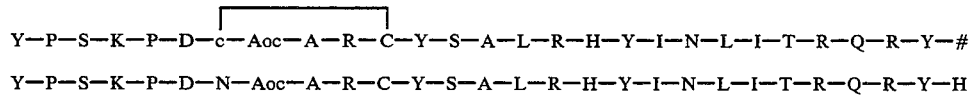

Y—P—S—Aoc—R—H—Y—I—N—L—I—T—R—Q—R—Y—#.

9. A method of activating a neuropeptide Y receptor in a patient in need thereof which comprises contacting said receptor with a peptide derivative of any one of claims 1-8.

* * * * *